(12) United States Patent
Cho et al.

(10) Patent No.: US 8,425,399 B2
(45) Date of Patent: Apr. 23, 2013

(54) FOCUSING BOARD ASSEMBLY FOR MEDICAL IMAGING EQUIPMENT

(75) Inventors: Moo-Seong Cho, Daegu (KR); Tae-Kwan Yun, Daegu (KR); Jae-Young Bae, Daegu (KR); Byung-Ki Kim, Daegu (KR); Soong-Hyuck Suh, Daegu (KR); Kyung-Chan Kim, Daegu (KR)

(73) Assignee: Industry-Academic Cooperation Foundation, Keimyung University, Dalseo-Gu (KR)

( * ) Notice: Subject to any disclaimer, the term of this patent is extended or adjusted under 35 U.S.C. 154(b) by 987 days.

(21) Appl. No.: 12/481,634

(22) Filed: Jun. 10, 2009

(65) Prior Publication Data

US 2010/0317915 A1    Dec. 16, 2010

(51) Int. Cl.
*A61M 21/00*  (2006.01)
*A61B 5/05*  (2006.01)

(52) U.S. Cl.
USPC ............................................. 600/27; 600/410

(58) Field of Classification Search .............. 600/26–28, 600/410, 418
See application file for complete search history.

(56) References Cited

U.S. PATENT DOCUMENTS

| | | | |
|---|---|---|---|
| 7,942,535 B2* | 5/2011 | Kjaer | 353/84 |
| 2005/0030659 A1* | 2/2005 | Asakawa | 359/892 |
| 2007/0086098 A1* | 4/2007 | Sekiguchi et al. | 359/892 |
| 2009/0059407 A1* | 3/2009 | Ho et al. | 359/892 |

* cited by examiner

*Primary Examiner* — John Lacyk
(74) *Attorney, Agent, or Firm* — Edwards Wildman Palmer LLP

(57) ABSTRACT

A focusing board assembly for a medical imaging equipment gives a comfortable feeling mentally or physically by visually getting rid of an oppressive feeling arisen when a patient is in a tunnel-like enclosed space such as MRI or CT for his/her medical examination.

10 Claims, 7 Drawing Sheets

FOCUSING BOARD ASSEMBLY FOR MEDICAL IMAGING EQUIPMENT

TECHNICAL FIELD

The present invention relates to a focusing board assembly for a medical imaging equipment, and more particularly, to a focusing board assembly for a medical imaging equipment that reduces an oppressive feeling arisen when a patient is in a tunnel-like enclosed space such as MRI or CT for his/her medical examination.

BACKGROUND ART

An medical imaging equipment used to diagnose various diseases of human body is largely divided into a magnetic resonance imaging (MRI), a computer tomography (CT), and a positron emission tomography (PET).

To scan an affected part using the medical imaging equipment, patients should lie in a monochromatic and narrow space of a bow for a long time. The patients feel as if they are heavily burdened, causing panic disorder. In some cases, some patients deny themselves to the medical examination. Claustrophobia makes the above-mentioned symptoms severer.

In order to solve the problems, various attempts have been made to make patients feel comfortable, for example, by using a mirror or an aromatic, or by providing music or movies with special glasses. However, most of the attempts were costly or insufficiently effective.

SUMMARY OF DISCLOSURE

The present invention is designed to solve the problems of the prior art, and therefore it is an object of the present invention to provide a focusing board assembly for a medical imaging equipment that gives a comfortable feeling mentally or physically by visually getting rid of an oppressive feeling arisen in a tight or enclosed space.

In order to accomplish the above object, the present invention provides a focusing board assembly for a medical imaging equipment, comprising: a focusing board installed at an inner periphery of a hollow bow, and having a predetermined color or pattern; a cover installed under the focusing board, and having an opening of a predetermined size; and a rotating means configured to selectively rotate any one of the focusing board and the cover, wherein when any one of the focusing board and the cover is rotated by the rotating means, the color or pattern on the focusing board is sequentially shown through the opening.

Preferably, the focusing board and the cover are installed to a support member installed at the inner periphery of the bow such that any one of the focusing board and the cover is rotatably installed to the support member and the other is fixed to the support member. The rotating means includes a plurality of protrusions arranged at a predetermined interval on any one rotatably installed among the focusing board and the cover; and a jet unit configured to selectively jet air to the protrusions, wherein any one of the focusing board and the cover is rotated by the air jetted from the jet unit to the protrusions.

Preferably, among the focusing board and the cover, the focusing board is rotated, and the rotating means includes a rotary motor unit installed at an end of the bow in a lengthwise direction of the bow or outside of the bow not to influence a magnetic field of the medical imaging equipment; and a rotary shaft configured to receive the driving force from the rotary motor unit to rotate the focusing board.

Preferably, a guide groove or rail is formed at the inner periphery of the bow along a lengthwise direction of the bow, and a support member is slidably installed to the guide groove or rail. The focusing board and the cover are installed to the support member such that any one of the focusing board and the cover is rotatably installed to the support member and the other is fixed to the support member.

Meanwhile, a focusing board assembly for a medical imaging equipment according to the present invention comprises a support installed at a hollow bow, and having a space therein where a movable bed is located or movable; a focusing board installed to the support, and having a predetermined color or pattern; a cover installed under the focusing board, and having an opening of a predetermined size; and a rotating means configured to selectively rotate any one of the focusing board and the cover, wherein when any one of the focusing board and the cover is rotated by the rotating means, the color or pattern on the focusing board is sequentially shown through the opening.

Preferably, the support is formed of a circular arc in contact with the inner periphery of the bow, and the opposite ends of the circular arc are supported by a holding means installed at a bottom of the medical imaging equipment so as to fix the support to the inner periphery of the bow.

Here, the focusing board and the cover are installed to a support member installed at the inner periphery of the support such that any one of the focusing board and the cover is rotatably installed to the support member and the other is fixed to the support member. The rotating means includes a plurality of protrusions arranged at a predetermined interval on any one installed rotatably among the focusing board and the cover; and a jet unit configured to selectively jet air to the protrusions, wherein any one of the focusing board and the cover is rotated by the air jetted from the jet unit to the protrusions.

And, a guide groove or rail is formed at the inner periphery of the support along a lengthwise direction of the support, and a support member is slidably installed to the guide groove or rail. Preferably, the focusing board and the cover are installed to the support member such that any one of the focusing board and the cover is rotatably installed to the support member and the other is fixed to the support member.

Further, among the focusing board and the cover, the focusing board is rotated. Preferably, the rotating means includes a rotary motor unit installed at an end of the bow in a lengthwise direction of the bow or outside of the bow not to influence a magnetic field of the medical imaging equipment; and a rotary shaft configured to receive the driving force from the rotary motor unit to rotate the focusing board.

DETAILED DESCRIPTION

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 1:
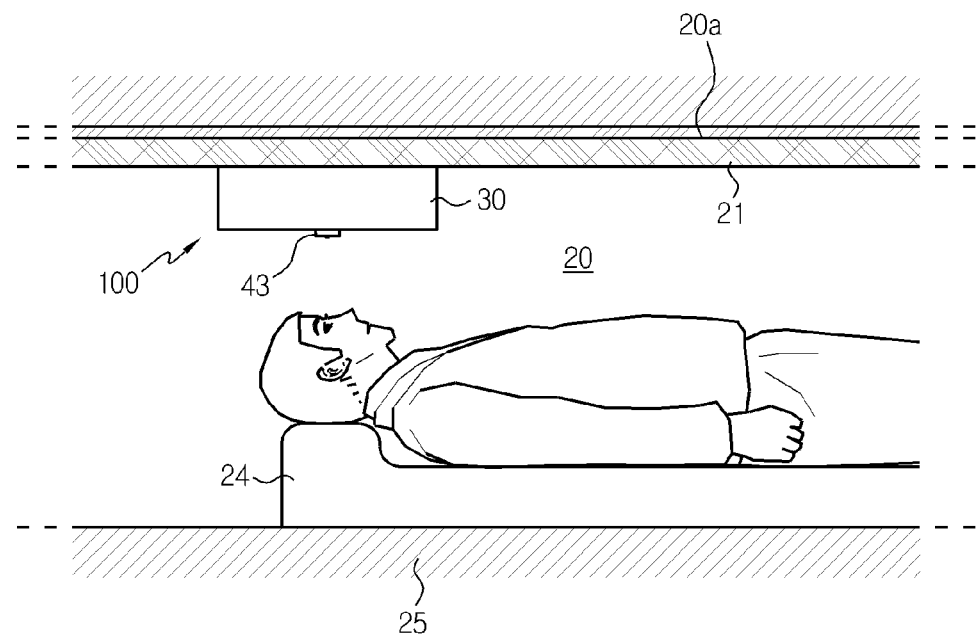
FIG. 1 is a cross-sectional side view of a medical imaging equipment with a focusing board assembly according to a preferred embodiment of the present invention.
Figure 2:
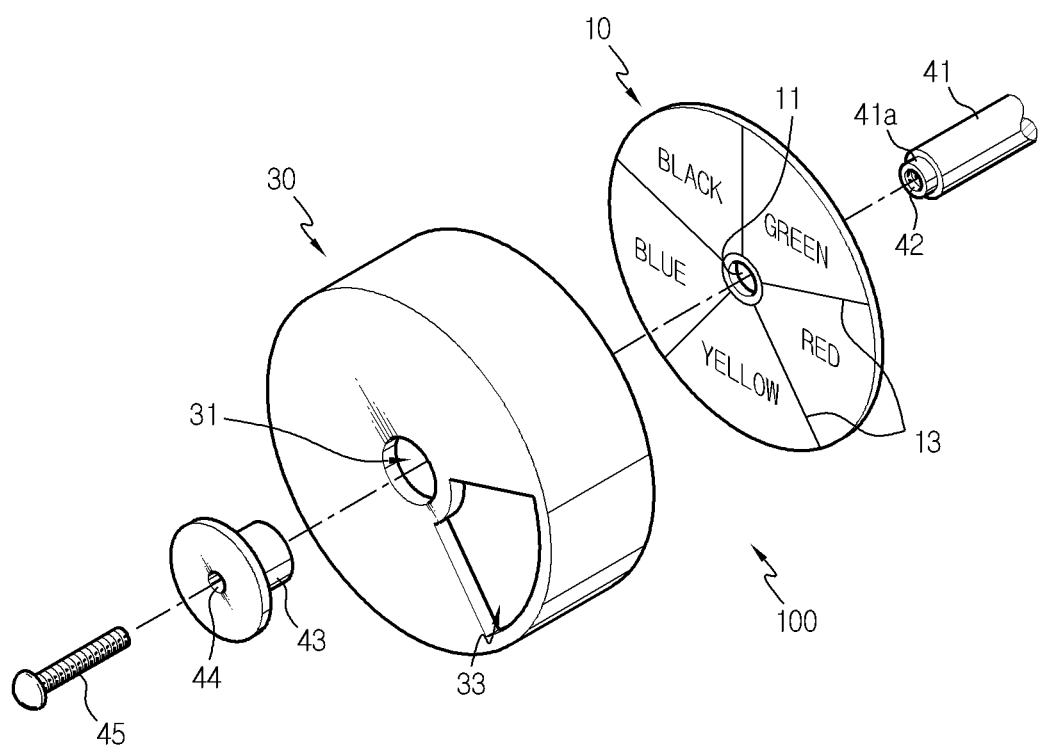
FIG. 2 is an exploded perspective view of the focusing board assembly of FIG. 1.
Figure 3:
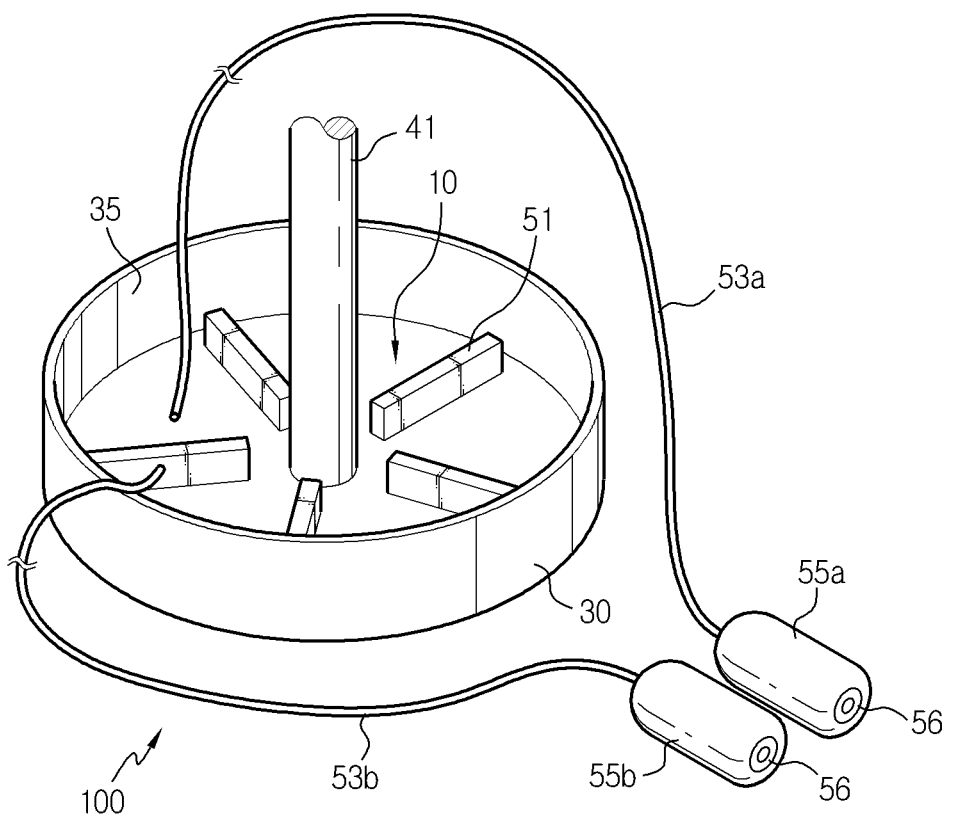
FIG. 3 is a perspective view of the focusing board assembly of FIG. 1.

FIG. 1 is a cross-sectional side view of a medical imaging equipment with a focusing board assembly according to a preferred embodiment of the present invention. FIG. 2 is an exploded perspective view of the focusing board assembly of FIG. 1. FIG. 3 is a perspective view of the focusing board assembly of FIG. 1.

Referring to FIGS. 1 to 3, the focusing board assembly 100 includes a focusing board 10, a cover 30 installed under the focusing board 10, and a rotating means for selectively rotating the focusing board 10.

The focusing board 10 is a flat plate having a predetermined color on its front surface. In FIG. 2, five colors, for example, green, red, yellow, blue and black are arranged at a predetermined angle. However, if it provides a comfortable feeling to a patient under examination, there is no limitation in aspect of the number, type or arrangement order of color on the focusing board 10.

And, the focusing board 10 may have a pattern on its front surface. Hereinafter, for the convenience of description, description is made based on the focusing board 10 having color arranged at a predetermined angle. Meanwhile, the pattern used in the specification includes a picture, a design and so on.

The focusing board 10 has a first through hole 11, and protrusions 51 arranged on its back surface at a predetermined interval. The first through hole 11 and the protrusions 51 will be described later.

The cover 30 is installed under the focusing board 10. The cover 30 has a second through hole 31 formed in the center thereof and an opening 33 formed near the second through hole 31. A support member is inserted into the second through hole 31.

The opening 33 goes though the cover 30 to show the color of the focusing board 10. Preferably, the opening 33 has such size and shape to wholly show a color area. For example, the opening 33 may have such size and shape to wholly show a green area and screen the other color areas.

The support member is inserted into the first and second through holes 11 and 31.

Figure 4:
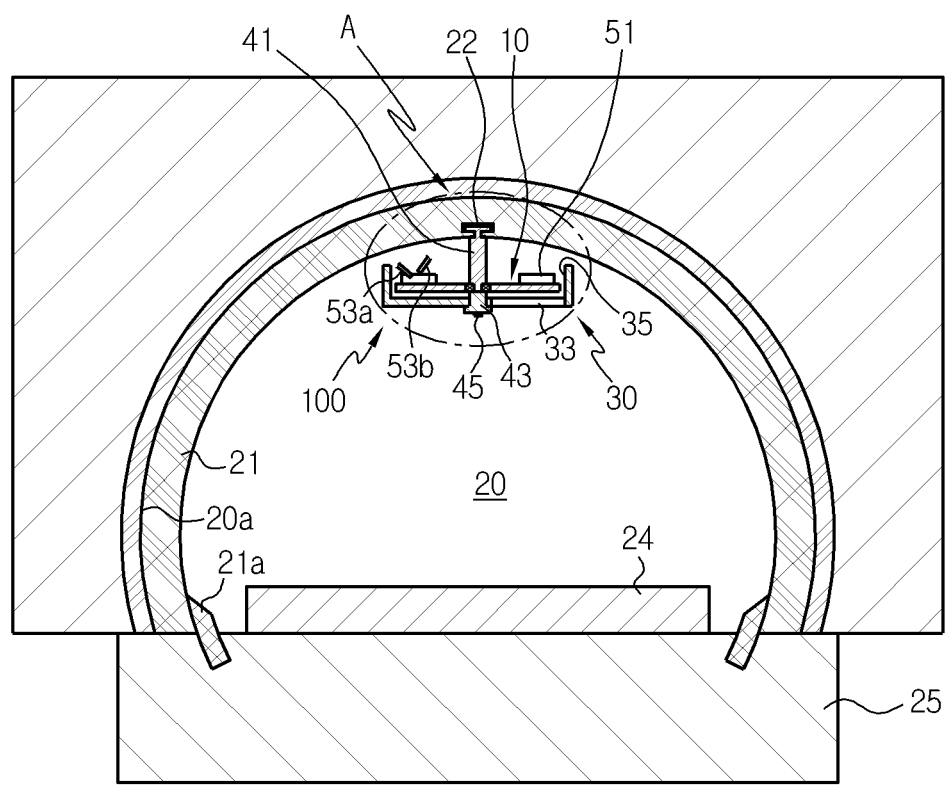
FIG. 4 is a cross-sectional front view of the medical imaging equipment with the focusing board assembly of FIG. 1.
Figure 5:
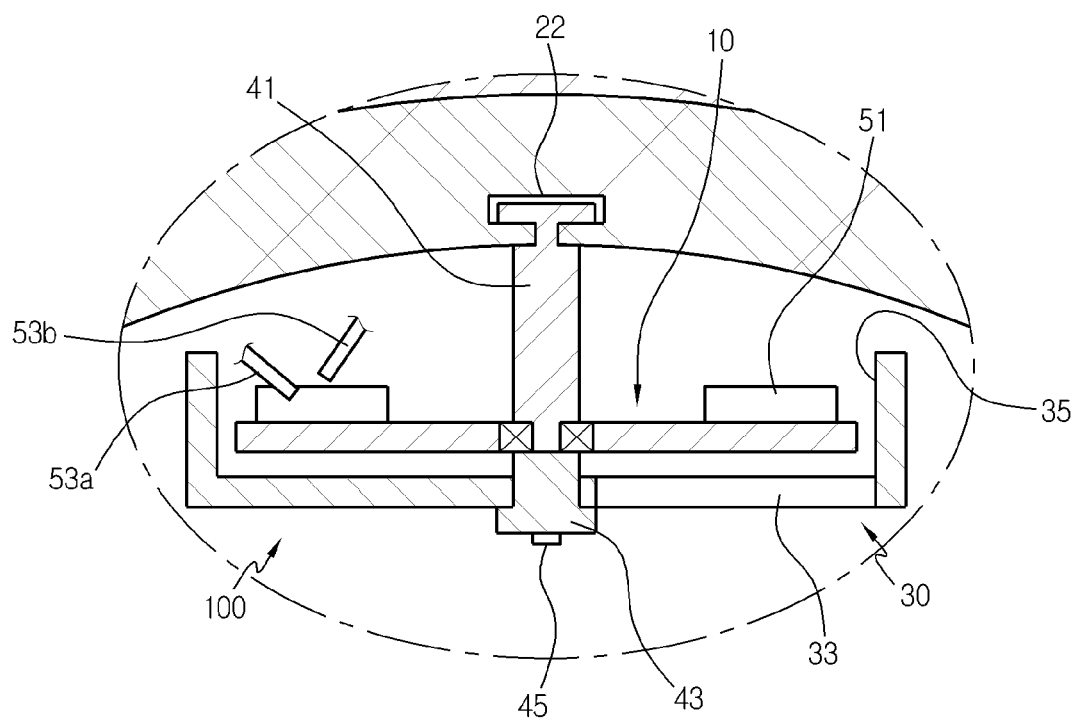
FIG. 5 is an enlarged view of section A of FIG. 4.

Preferably, the support member includes a first support member 41 penetrating the first through hole 11, a second support member 43 penetrating the second through hole 31, and a bolt 45 for fastening the first and second support members 41 and 43. As shown in FIGS. 4 and 5, the first support member 41 has a stepped end 41a that is inserted into the first through hole 11.

The first support member 41 and the second support member 43 are connected with each other at their ends. The diameter of the end of the second support member 43 is larger than the diameter of the end of the first support member 41. Thus, the focusing board 10 is rotatably supported by the end of the second support member 43. Meanwhile, the first through hole 11 has a non-metal bearing (hereinafter referred to as 'a bearing') to provide better rotation to the focusing board 10.

The first and second support members 41 and 43 have holes 42 and 44, respectively. The bolt 45 is inserted into the holes 42 and 44 to connect the first and second support members 41 and 43.

The rotating means selectively rotates the focusing board 10. The rotating means includes the protrusions 51 provided on the back surface of the focusing board 10, and a jet unit configured to selectively jet air to the protrusions 51.

Preferably, the protrusions 51 are located at areas corresponding to boundaries 13 between each color area of the focusing board 10. Using the protrusions 51, the focusing board 10 is stopped after rotation, so that each color area (for example, a green area) is location at the opening 33 and wholly shown through the opening 33.

The jet unit includes hoses 53a and 53b, and air bags 55a and 55b for supplying air to the hoses 53a and 53b. The air bags 55a and 55b are formed of an elastically restorable material. The air bags 55a and 55b, when pressed down, jet air contained therein to the protrusions 51 through the hoses 53a and 53b. The air jetted to the protrusions 51 rotates the focusing board 10 or stops the rotating focusing board 10.

More preferably, the air bags 55a and 55b include a first air bag 55a connected with the first hose 53a, and a second air bag 55b connected with the second hose 53b. The first and second air bags 55a and 55b are preferably located at the opposite sides of the protrusion 51. The first air bag 55a jets air through the first hose 53a to rotate the focusing board 10 and then the second air bag 55b jets air through the second hose 53b to stop the rotating focusing board 10.

The hoses 53a and 53b are guided by a guide member (not shown) installed to a support 21. The guide member guides the hoses 53a and 53b such that one ends of the hoses 53a and 53b face the protrusions 51.

Preferably, each of the air bags 55a and 55b has a check valve 56. The check valve 56 permits the external air to flow into the air bags 55a and 55b while the deformed air bags 55a and 55b restore to their original shape, and the internal air to be discharged only through the hoses 53a and 53b while the air bags 55a and 55b are pressed down. The check valve 56 is generally used to allow fluid to flow in one direction, and thus its detailed description is omitted herein.

According to the present invention, the focusing board 10 may be installed at the support 21. The support 21 defines a hollow bow 20. The support 21 is a structure having a cross section of a circular arc, and has an internal space where a movable bed 24 is located or movable. Preferably, the support 21 has the same curvature as an inner periphery 20a of the bow 20 and is in contact with the inner periphery 20a of the bow 20.

Preferably, the support 21 is made of a material that protects against outer shocks and defects, provides elastic restitution and transparency, and is less affected by temperature and thus is resistant against deformation with temperature. The material satisfying the above-mentioned properties includes acryl and so on.

Preferably, the support 21 has a shape of a circular arc in contact with the inner periphery 20a of the bow 20. The opposite ends of the circular arc are supported by a holding member 21a. The holding member 21a is installed at a bottom 25 of the medical imaging equipment and fixes the support 21 such that the support 21 is in contact with the inner periphery 20a of the bow 20.

Preferably, the support 21 has a guide groove 22 extending in a lengthwise direction thereof. As shown in FIG. 5, the guide groove 22 is configured to guide the first support member 41 to slide along the lengthwise direction of the support 21. If the first support member 41 can move along the lengthwise direction of the support 21, it is possible to move the focusing board assembly 100 depending on the position of a patient lying on the bed of the medical imaging equipment.

Meanwhile, the guide grove 22 may be formed at the inner periphery 20a of the bow 20. That is, even though the support 21 is not installed, the first support member 41 can move along the lengthwise direction of the bow 20.

Moreover, a rail (not shown) may be installed at the support 21 or the inner periphery 20a of the bow 20, instead of the guide groove 22. That is, in the case that a rail is installed at the support 21 or the inner periphery 20a of the bow 20, the first support member 41 can slide along the rail.

Although this embodiment shows the focusing board 10 is rotated by the rotating means and the cover 30 is fixed, the present invention is not limited in this regard. For example, the focusing board 10 may be fixed to the support member, and the cover 30 may be rotatably installed to the support member (for example, by setting a bearing into the second through hole 31), so that the cover 30 can be rotated by the rotating means. In this case, the protrusions 51 are formed on the cover 30, in particular, the inner periphery (35 of FIGS. 3 to 5) of the cover 30. And, the hoses 53a and 53b are installed facing the protrusions 51. For example, each hose is installed at the opposite sides of the protrusion 51. Air jetted from the hoses 53a and 53b is dashed against the protrusions 51, and the stopped cover 30 is then rotated or the rotating cover 30 is stopped.

Figure 6:
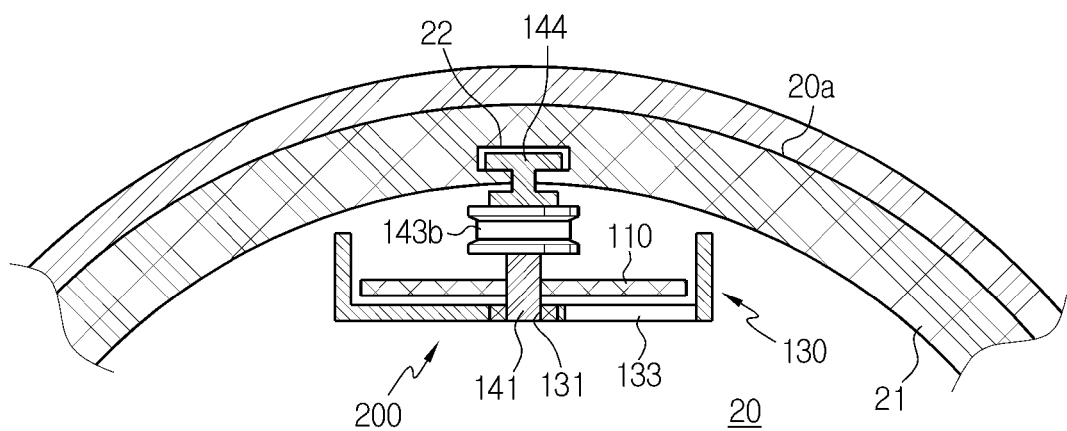
FIG. 6 is a partially cross-sectional front view of a medical imaging equipment with a focusing board assembly according to another preferred embodiment of the present invention.
Figure 7:
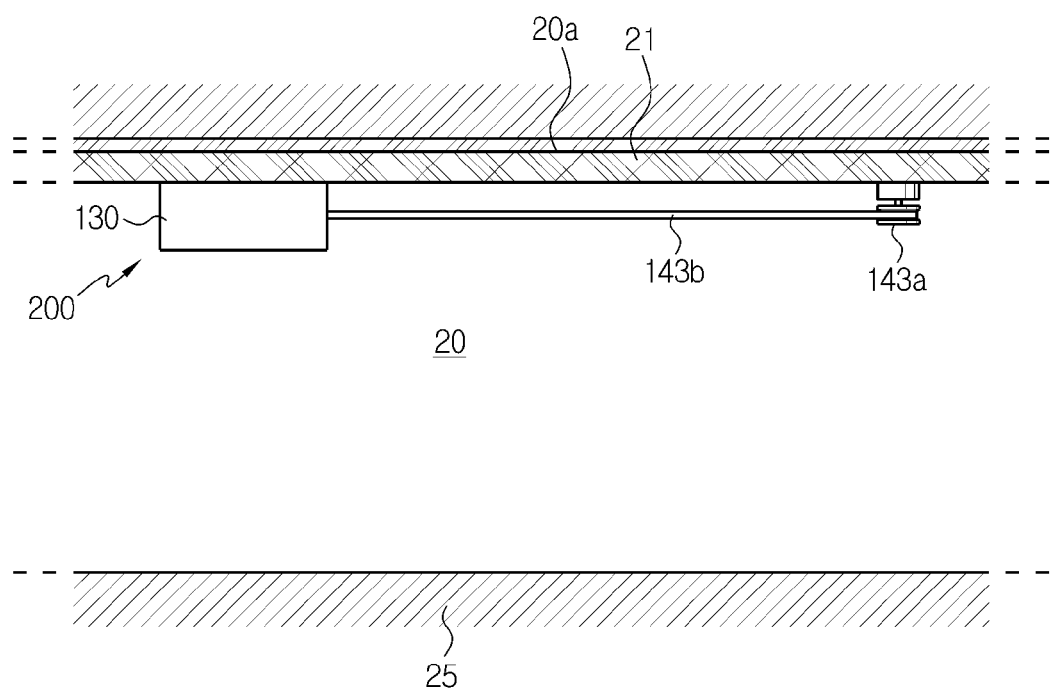
FIG. 7 is a cross-sectional side view of the medical imaging equipment with the focusing board assembly of FIG. 6.

FIG. 6 is a partially cross-sectional front view of a medical imaging equipment with a focusing board assembly according to another preferred embodiment of the present invention. FIG. 7 is a cross-sectional side view of the medical imaging equipment with the focusing board assembly of FIG. 6.

The focusing board assembly 200 includes a support 21, a rotating means installed to the support 21, a focusing board 110 rotated by the rotating means, and a cover 130 installed under the focusing board 110. The focusing board assembly 200 is characterized by the rotation of the focusing board 110 by a rotary motor 143a. The support 21 of this embodiment is the same as that of the above-mentioned embodiment, and its description is omitted herein.

The rotating means includes a rotary shaft 141, and a rotary motor unit configured to rotate the rotary shaft 141.

The rotary motor unit includes the rotary motor 143a, a belt 143b configured to transmit a driving force between the rotary motor 143a and the rotary shaft 141, and an engaging part 144 connected with the rotary shaft 141 and fitted in a guide groove 22. The rotary motor 143a generates a magnetic field. Preferably, the rotary motor 143a is installed at an end of the bow 20 in the lengthwise direction of the bow 20 or outside of the bow 20 so as not to influence a magnetic field of the medical imaging equipment.

The driving force of the rotary motor 143a is transmitted to the rotary shaft 141 through the belt 143b. The rotation rate (R.P.M) of the rotary motor 143a may be controlled by a patient under examination, or an engineer or a doctor positioned outside of the bow 20. A configuration for controlling the rotation rate (R.P.M) of the rotary motor 143a is well known to an ordinary person skilled in the art, and its description is omitted herein.

The cover 130 is located under the focusing board 10 to cover the focusing board 10. The cover 130 has an opening 133 of a predetermined size and a second through hole 131. The opening 133 of this embodiment is the same as that of the above-mentioned embodiment. The rotary shaft 141 goes through the second through hole 131. For better rotation, the second through hole 131 has preferably a bearing.

Although this embodiment shows the focusing board 110 is rotated by the rotary shaft 141 and the cover 130 is fixed, the present invention is not limited in this regard. For example, the focusing board 110 may be fixed to the support 21, and the cover 130 may be rotated by the rotary shaft 141. In this case, the focusing board 10 has a first through hole in the center thereof, through which the rotary shaft 141 goes. And, the first through hole has a larger diameter than the rotary shaft 141, so that the focusing board 10 is not influenced by rotation of the rotary shaft 141.

According to the present invention, the focusing board assembly for the medical imaging equipment has the following effects.

When a patient is examined in an enclosed space of the medical imaging equipment for a long time, the patient naturally focuses his/her eyes on the focusing board. Then, the patient does not recognize an internal space of a bow as an enclosed space, but as a mentally comfortable space.

Further, the patient can directly manipulate the focusing board, and thus does not feel bored even though the examination proceeds for a long time.

What is claimed is:

1. A focusing board assembly for a medical imaging equipment, comprising:
   a focusing board installed to an inner periphery of a hollow bow, and having a predetermined color or pattern;
   a cover installed under the focusing board, and having an opening of a predetermined size; and
   a rotating means configured to selectively rotate any one of the focusing board and the cover,
   wherein when any one of the focusing board and the cover is rotated by the rotating means, the color or pattern on the focusing board is sequentially shown through the opening, and
   wherein the focusing board and the cover are installed to a support member installed at the inner periphery of the bow such that any one of the focusing board and the cover is rotatably installed to the support member and the other is fixed to the support member, and
   wherein the rotating means includes:
   a plurality of protrusions arranged at a predetermined interval on any one rotatably installed among the focusing board and the cover; and
   a jet unit configured to selectively jet air to the protrusions,
   wherein any one of the focusing board and the cover is rotated by the air jetted from the jet unit to the protrusions.

2. A focusing board assembly for a medical imaging equipment, comprising:
   a focusing board installed to an inner periphery of a hollow bow, and having a predetermined color or pattern;
   a cover installed under the focusing board, and having an opening of a predetermined size; and
   a rotating means configured to selectively rotate any one of the focusing board and the cover,
   wherein when any one of the focusing board and the cover is rotated by the rotating means, the color or pattern on the focusing board is sequentially shown through the opening, and wherein a guide groove or rail is formed at the inner periphery of the bow along a lengthwise direction of the bow, and a support member is slidably installed to the guide groove or rail, and wherein the focusing board and the cover are installed to the support member such that any one of the focusing board and the cover is rotatably installed to the support member and the other is fixed to the support member.

3. A focusing board assembly for a medical imaging equipment, comprising:
    a support installed to an inner periphery of a hollow bow, and having a space therein where a movable bed is located or movable;
    a focusing board installed to the support, and having a predetermined color or pattern;
    a cover installed under the focusing board, and having an opening of a predetermined size; and
    a rotating means configured to selectively rotate any one of the focusing board and the cover,
    wherein when any one of the focusing board and the cover is rotated by the rotating means, the color or pattern on the focusing board is sequentially shown through the opening.

4. The focusing board assembly for a medical imaging equipment according to claim 3,
    wherein the support is formed of a circular arc in contact with the inner periphery of the bow, and
    wherein the opposite ends of the circular arc are supported by a holding means to fix the support to the inner periphery of the bow, the holding means being installed at a bottom of the medical imaging equipment.

5. The focusing board assembly for a medical imaging equipment according to claim 3,
    wherein the focusing board and the cover are installed to a support member installed at an inner periphery of the support such that any one of the focusing board and the cover is rotatably installed to the support member and the other is fixed to the support member, and
    wherein the rotating means includes:
    a plurality of protrusions arranged at a predetermined interval on any one rotatably installed among the focusing board and the cover; and
    a jet unit configured to selectively jet air to the protrusions,
    wherein any one of the focusing board and the cover is rotated by the air jetted from the jet unit to the protrusions.

6. The focusing board assembly for a medical imaging equipment according to claim 3,
    wherein a guide groove or rail is formed at an inner periphery of the support along a lengthwise direction of the support, and a support member is slidably installed to the guide groove or rail, and
    wherein the focusing board and the cover are installed to the support member such that any one of the focusing board and the cover is rotatably installed to the support member and the other is fixed to the support member.

7. The focusing board assembly for a medical imaging equipment according to claim 3,
    wherein among the focusing board and the cover, the focusing board is rotated, and
    wherein the rotating means includes:
    a rotary motor unit installed at an end of the bow in a lengthwise direction of the bow or outside of the bow not to influence a magnetic field of the medical imaging equipment; and
    a rotary shaft configured to receive the driving force from the rotary motor unit to rotate the focusing board.

8. The focusing board assembly for a medical imaging equipment according to claim 4,
    wherein the focusing board and the cover are installed to a support member installed at an inner periphery of the support such that any one of the focusing board and the cover is rotatably installed to the support member and the other is fixed to the support member, and
    wherein the rotating means includes:
    a plurality of protrusions arranged at a predetermined interval on any one rotatably installed among the focusing board and the cover; and
    a jet unit configured to selectively jet air to the protrusions,
    wherein any one of the focusing board and the cover is rotated by the air jetted from the jet unit to the protrusions.

9. The focusing board assembly for a medical imaging equipment according to claim 4,
    wherein a guide groove or rail is formed at an inner periphery of the support along a lengthwise direction of the support, and a support member is slidably installed to the guide groove or rail, and
    wherein the focusing board and the cover are installed to the support member such that any one of the focusing board and the cover is rotatably installed to the support member and the other is fixed to the support member.

10. The focusing board assembly for a medical imaging equipment according to claim 4,
    wherein among the focusing board and the cover, the focusing board is rotated, and
    wherein the rotating means includes:
    a rotary motor unit installed at an end of the bow in a lengthwise direction of the bow or outside of the bow not to influence a magnetic field of the medical imaging equipment; and
    a rotary shaft configured to receive the driving force from the rotary motor unit to rotate the focusing board.

* * * * *